US009778225B2

(12) United States Patent
Wang et al.

(10) Patent No.: US 9,778,225 B2
(45) Date of Patent: Oct. 3, 2017

(54) MAGNETIC SEARCH COIL FOR MEASURING REAL-TIME BROWNIAN RELAXATION OF MAGNETIC NANOPARTICLES

(75) Inventors: Jian-Ping Wang, Shoreview, MN (US); Liang Tu, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 936 days.

(21) Appl. No.: 13/885,384

(22) PCT Filed: Nov. 15, 2011

(86) PCT No.: PCT/US2011/060837
§ 371 (c)(1),
(2), (4) Date: Dec. 23, 2013

(87) PCT Pub. No.: WO2012/068146
PCT Pub. Date: May 24, 2012

(65) Prior Publication Data
US 2014/0097829 A1    Apr. 10, 2014

Related U.S. Application Data

(60) Provisional application No. 61/413,884, filed on Nov. 15, 2010.

(51) Int. Cl.
*G01R 33/12* (2006.01)
*G01N 27/72* (2006.01)

(52) U.S. Cl.
CPC ............ *G01N 27/72* (2013.01); *G01R 33/12* (2013.01); *G01R 33/1269* (2013.01); *G01R 33/1276* (2013.01)

(58) Field of Classification Search
CPC .......................... G01R 33/12; G01R 33/1269; G01R 33/1276; G01N 27/72
(Continued)

(56) References Cited

U.S. PATENT DOCUMENTS 5,089,781 A * 2/1992 Arichika ................ G01R 27/22
324/204
5,315,243 A * 5/1994 Kempster .......... G01N 15/0656
324/204
(Continued)

FOREIGN PATENT DOCUMENTS

WO    WO-03019188 A1    3/2003
WO    WO-2009013668 A2    1/2009
(Continued)

OTHER PUBLICATIONS

"International Application Serial No. PCT/US2011/060828, International Search Report Feb. 2, 2012", 4 pgs.
(Continued)

*Primary Examiner* — Jay Patidar
(74) *Attorney, Agent, or Firm* — Schwegman Lundberg & Woessner, P.A.

(57) ABSTRACT

A device includes an excitation coil, a detector coil, and a processing circuit. The excitation coil is aligned about a volume. The excitation coil is configured to carry a first and second biasing current and generate a magnetic field in the volume. The detector coil is configured to generate an electrical signal based on a detected field within the volume. The detected field is based on the magnetic field. The processing circuit is configured to generate data based on the electrical signal.

17 Claims, 11 Drawing Sheets

(58) Field of Classification Search
USPC .......................................................... 324/204
See application file for complete search history.

(56) References Cited

U.S. PATENT DOCUMENTS

| | | | |
|---|---|---|---|
| 5,444,367 A * | 8/1995 | Kempster | G01N 15/0656 |
| | | | 324/204 |
| 5,548,214 A * | 8/1996 | Yasohama | G01N 27/9086 |
| | | | 324/228 |
| 5,608,315 A | 3/1997 | Crayton et al. | |
| 5,655,665 A | 8/1997 | Allen et al. | |
| 5,793,199 A * | 8/1998 | Kasahara | G01N 15/0656 |
| | | | 324/204 |
| 5,981,297 A | 11/1999 | Baselt | |
| 6,046,585 A * | 4/2000 | Simmonds | B82Y 15/00 |
| | | | 324/204 |
| 6,057,167 A | 5/2000 | Shieh et al. | |
| 6,468,809 B1 | 10/2002 | Prinz et al. | |
| 6,510,031 B1 | 1/2003 | Gambino et al. | |
| 6,592,820 B1 | 7/2003 | Hardman et al. | |
| 6,736,978 B1 | 5/2004 | Porter et al. | |
| 6,743,639 B1 | 6/2004 | Tondra et al. | |
| 7,106,051 B2 | 9/2006 | Prins et al. | |
| 7,470,540 B2 | 12/2008 | Stähler et al. | |
| 7,651,871 B2 | 1/2010 | Sharma | |
| 7,729,093 B1 | 6/2010 | Zhou | |
| 8,084,270 B2 | 12/2011 | Prins et al. | |
| 9,023,651 B2 | 5/2015 | Evers et al. | |
| 9,091,688 B2 | 7/2015 | Bangert et al. | |
| 9,176,206 B2 | 11/2015 | Wang et al. | |
| 2001/0050555 A1 | 12/2001 | Hawkins et al. | |
| 2002/0060565 A1 | 5/2002 | Tondra | |
| 2003/0169032 A1* | 9/2003 | Minchole | B82Y 25/00 |
| | | | 324/204 |
| 2004/0023365 A1 | 2/2004 | Engel et al. | |
| 2004/0033627 A1 | 2/2004 | Aytur et al. | |
| 2004/0137275 A1 | 7/2004 | Jander et al. | |
| 2005/0087000 A1 | 4/2005 | Coehoorn et al. | |
| 2005/0106758 A1 | 5/2005 | Fukumoto et al. | |
| 2005/0170418 A1 | 8/2005 | Moreland et al. | |
| 2006/0019373 A1 | 1/2006 | Kahlman et al. | |
| 2006/0020371 A1 | 1/2006 | Ham et al. | |
| 2006/0214658 A1 | 9/2006 | Kahlman | |
| 2007/0063695 A1 | 3/2007 | Ruhrig et al. | |
| 2007/0155024 A1* | 7/2007 | Miethe | G01N 27/745 |
| | | | 436/524 |
| 2007/0172890 A1 | 7/2007 | Prins et al. | |
| 2007/0197900 A1 | 8/2007 | Baudenbacher et al. | |
| 2008/0014651 A1 | 1/2008 | Bangert | |
| 2008/0032423 A1 | 2/2008 | Wang et al. | |
| 2008/0054892 A1* | 3/2008 | Skultety-Betz | G01V 3/107 |
| | | | 324/228 |
| 2008/0185043 A1 | 8/2008 | Prins et al. | |
| 2008/0206104 A1 | 8/2008 | Prins et al. | |
| 2008/0206892 A1 | 8/2008 | Prins | |
| 2008/0258721 A1 | 10/2008 | Guo et al. | |
| 2008/0261329 A1* | 10/2008 | Nikitin | G01N 27/745 |
| | | | 436/526 |
| 2008/0309329 A1 | 12/2008 | Kahlman et al. | |
| 2009/0085557 A1 | 4/2009 | Krozer et al. | |
| 2009/0224755 A1 | 9/2009 | Kahlman et al. | |
| 2009/0237844 A1 | 9/2009 | Duric et al. | |
| 2009/0243594 A1 | 10/2009 | Kahlman et al. | |
| 2009/0243603 A1 | 10/2009 | Mäkiranta et al. | |
| 2009/0267596 A1 | 10/2009 | Wang et al. | |
| 2010/0134097 A1 | 6/2010 | Wang et al. | |
| 2010/0213934 A1 | 8/2010 | Wang et al. | |
| 2010/0233822 A1 | 9/2010 | Prins | |
| 2011/0140688 A1* | 6/2011 | Yang | G01R 33/16 |
| | | | 324/201 |
| 2011/0207229 A1 | 8/2011 | Evers et al. | |
| 2012/0299584 A1* | 11/2012 | Kruusing | G01N 33/2888 |
| | | | 324/204 |
| 2014/0099663 A1 | 4/2014 | Wang et al. | |

FOREIGN PATENT DOCUMENTS

| | | |
|---|---|---|
| WO | WO-2009037636 A1 | 3/2009 |
| WO | WO-2010008478 A2 | 1/2010 |
| WO | WO-2012068139 A1 | 5/2012 |
| WO | WO-2012068146 A1 | 5/2012 |

OTHER PUBLICATIONS

"International Application Serial No. PCT/US2011/060828, Written Opinion mailed Feb. 2, 2012", 9 pgs.

"International Application Serial No. PCT/US2011/060837, International Search Report mailed Jan. 30, 2012", 4 pgs.

"International Application Serial No. PCT/US2011/060837, Written Opinion mailed Jan. 30, 2012", 9 pgs.

Krause, et al., "Magnetic particle detection by frequency mixing for immunoassay applications", Journal of Magnetism and Magnetic Materials vol. 311, No. 1, (Mar. 15, 2007), 436-444.

Nikitin, et al., "New type of biosensor based on magnetic nanoparticle detection", Journal of magnetism and magnetic materials vol. 311, No. 1, (Mar. 15, 2007), 445-449.

"U.S. Appl. No. 13/885,359, Non Final Office Action mailed Mar. 17, 2016", 11 pgs.

"U.S. Appl. No. 13/885,359, Response filed Jun. 27, 2016 Non Final Office Action mailed Mar. 17, 2016", 12 pgs.

"International Application Serial No. PCT/US2011/060828, International Preliminary Report on Patentability mailed May 30, 2013", 11 pgs.

"International Application Serial No. PCT/US2011/060837, International Preliminary Report on Patentability mailed May 30, 2013", 11 pgs.

"U.S. Appl. No. 13/885,359, Non Final Office Action mailed Aug. 3, 2016", 11 pgs.

"U.S. Appl. No. 13/885,359, Preliminary Amendment filed May 14, 2013", 6 pgs.

"U.S. Appl. No. 13/885,359, Response filed Dec. 5, 2016 to Non Final Office Action mailed Aug. 3, 2016", 16 pgs.

"U.S. Appl. No. 13/885,359, Response filed Dec. 5, 2016 to Non Final Office Action mailed Aug. 3, 2016", 18 pgs.

* cited by examiner

MAGNETIC SEARCH COIL FOR MEASURING REAL-TIME BROWNIAN RELAXATION OF MAGNETIC NANOPARTICLES

CLAIM OF PRIORITY

This patent application is a U.S. National Stage Filing under 35 U.S.C. 371 from International Application no. PCT/US2011/060837, filed on Nov. 15, 2011, and published as WO 2012/068146 A1 on 24 May 2012 which claims the benefit of priority to U.S. Provisional Patent Application Serial Number 61/413,884, entitled "MAGNETIC NANO-PARTICLE- BASED MAGNETIC COLORING," filed on Nov. 15, 2010, which applications and publication are incorporated herein by reference in their entirety.

CROSS-REFERENCE TO RELATED PATENT DOCUMENTS

This patent application is also related to Wang et. al, PCT Application Serial Number PCT/US2011/060828, entitled "GMR SENSOR," filed on Nov. 15, 2011.

STATEMENT REGARDING FEDERALLY SPONSORED RESEARCH OR DEVELOPMENT

This invention was made with government support under award number 1717-522-6686 from National Science Foundation. The government has certain rights in this invention.

BACKGROUND

Traditional methods for detecting magnetic susceptibility, such as AC magnetic susceptibility, are inadequate. Such methods suffer from high background fluctuation due to the thermal and mechanical instability of coils and from the magnetic moment contribution from sample matrix (e.g., water) or the container (e.g., plastic tube). Given the small amount of MNPs sample in the paramagnetic or diamagnetic environment, the background is a significant portion of the overall signal.

OVERVIEW

Real-time Brownian relaxation of magnetic nanoparticles (MNPs) can be detected by a mixing-frequency method. MNPs are driven into the saturation region by a low frequency sinusoidal magnetic field. A high frequency sinusoidal magnetic field is then applied to generate mixing-frequency signals that are highly specific to the magnetization of MNPs. The mixing-frequency signals from MNPs are picked up by a pair of balanced built-in detection coils. The phase delays of the mixing-frequency signals behind the applied field are determined.

Commercial iron oxide MNPs with a core diameter of 35 nm can be used for the measurement of Brownian relaxation. The results can be fitted with a Debye model. A real-time measurement of the binding process between protein G and its antibody can be demonstrated using MNPs as labels. The volume-based magnetic sensing technology herein can be used to detect binding kinetics and interaction affinities between biomolecules in real time.

An example of the present subject matter includes a mixing-frequency method to detect the nonlinear magnetization of MNPs per testing sample by measuring the amplitude of the mixing frequency signals and thereby avoid the high noise at the fundamental frequencies.

A magnetic field with low frequency (e.g., $f_2$=10 Hz) and large amplitude drives the MNPs into their nonlinear saturation region periodically. Another magnetic field with higher frequency (e.g., $f_1$=20 kHz), and with a relatively small amplitude due to the inductance of excitation coil, is used to transfer the nonlinearity into the mixing frequency signals, such as $f_1+2f_2$ (20.02 kHz). In this higher frequency region, the detection coil has higher output voltage This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
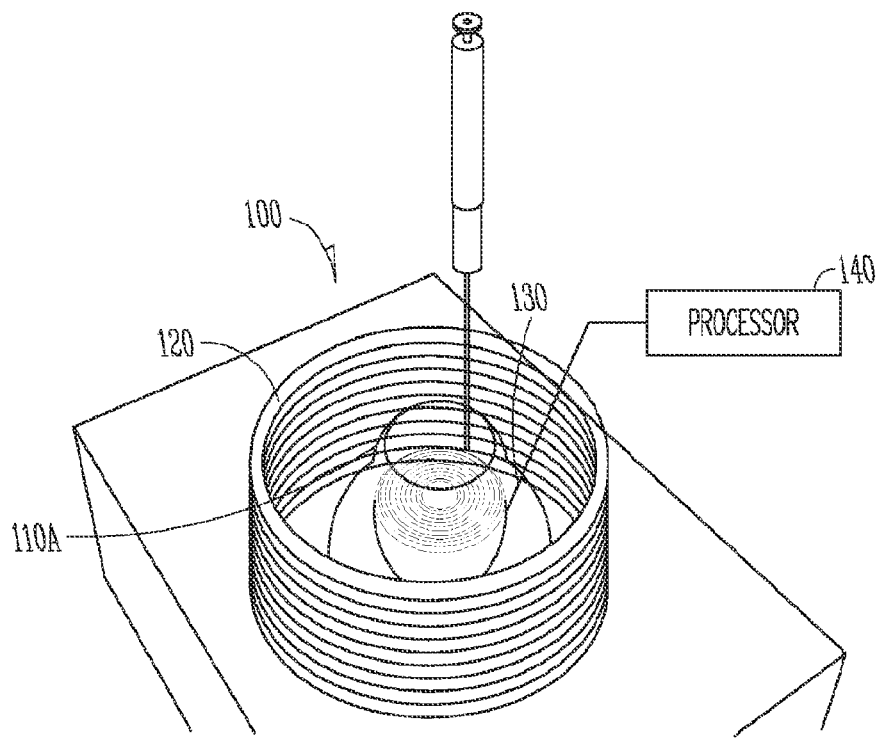
FIG. 1 illustrates a device, according to one example.

FIG. 1 illustrates device 100 (sometimes called a search coil), according to one example. Device 100 includes sample container 110A, excitation coil 120, detection coil 130, and processor 140.

Sample container 110A is configured to receive a fluid under test within a volume. The fluid can be delivered to device 100 by a channel having nanoscale, microscale or other dimensions.

Excitation coil 120 includes windings distributed about the volume. In one example, excitation coil 120 includes two independent windings that are separately energized. Excitation coil 120 is coupled to processor 140. In one example, excitation coil 120 includes two separate coils that generate 200 Hz field with 100 Oe field amplitude and 20 kHz field with 10 Oe field amplitude.

Detection coil 130 includes a sensitive coil configured to detect presence of a magnetic nanoparticle within the volume. In one example, detection coil 130 includes a pair of pick up coil is wound 500 rounds differentially.

In the example shown, processor 140 is coupled to detection coil 130 and also coupled to excitation coil 120. In one example, processor 140 is coupled to component of the fluid channel and is configured to control flow of sample materials to the sample container 110A.

Processor 140 can include an amplifier, an analog to digital converter, a signal processor, a transmitter, and other elements. Processor 140 can include an instrumentation amplifier configured to amplify a detected signal by 100 times. Processor 140 can include a digital acquisition card (DAQ) configured to sample the data at 1M sample/second with 14-bit resolution. Processor 140 can be configured to control other instruments and displays in real time or batch mode.

Figure 2:
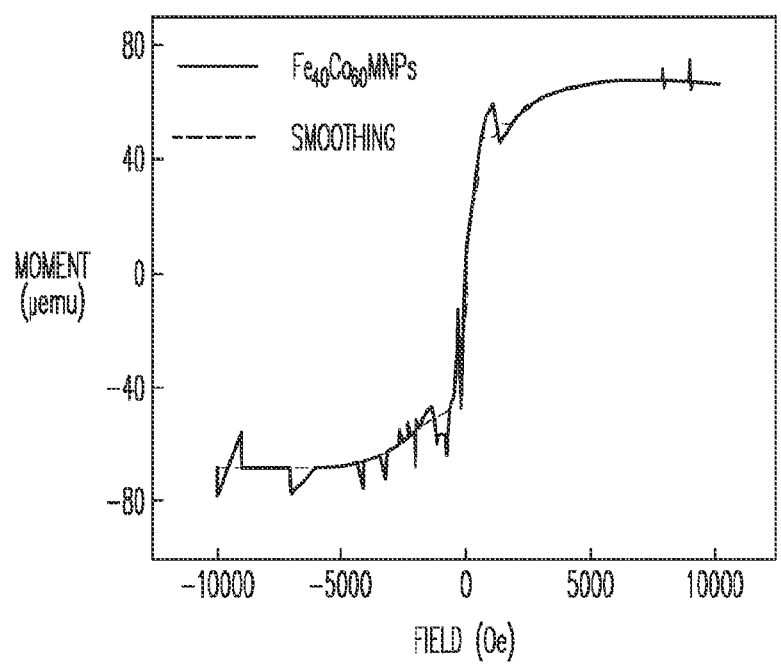
FIG. 2 illustrates an M-H loop for selected magnetic nanoparticles.

FIG. 2 illustrates an M-H loop of FeCo magnetic nanoparticles at room temperature as measured by a superconducting quantum interference device (SQUID).

According to one example, magnetic nanoparticles (MNPs) are driven into saturation region periodically by a strong ac field with a low frequency $f_2$. A second ac magnetic field, having a higher frequency $f_1$, is used to transfer the nonlinearity into the mixing frequency signals. Magnetization of MNPs is a Langevin function of H. The fourth term of magnetization Taylor expansion at zero field contains the mixing frequencies $f_1 \pm 2f_2$.

Figure 3:
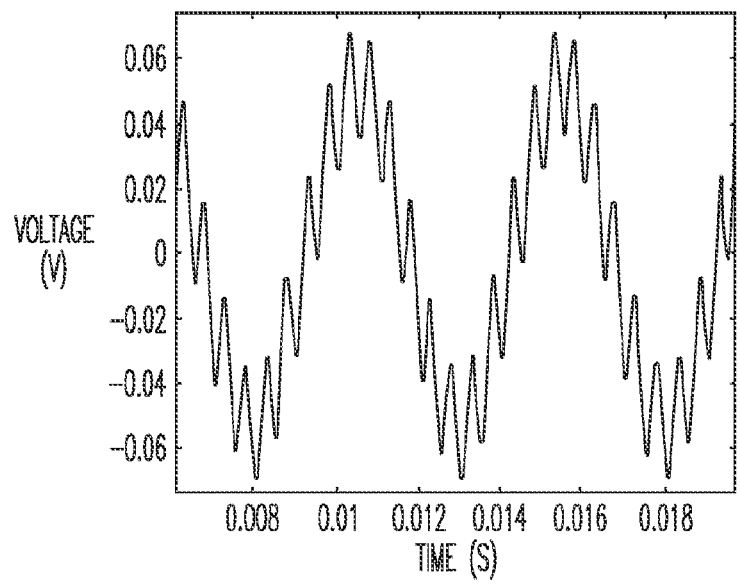
FIG. 3 illustrates detected signals in time domain, according to one example.
Figure 4:
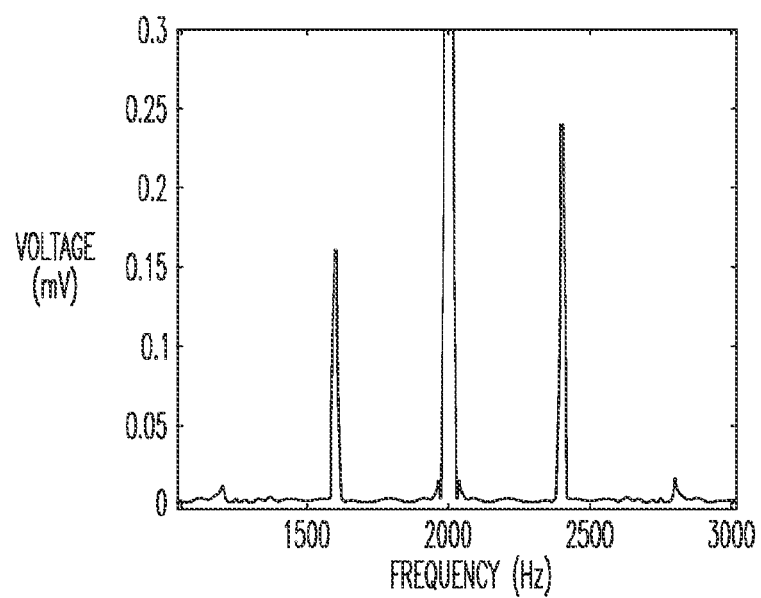
FIG. 4 includes detected signals in frequency domain, according to one example.

FIGS. 3 and 4 illustrate detected signals in the time domain and in the frequency domain. The harmonics apparent in the frequency domain shown in FIG. 4 indicate how the low frequency signal is transferred to a high frequency region, and thus avoids 1/f artifacts and measurement noise in the system.

In addition, detection of the mixing-frequency component can avoid the high background noises from fundamental frequencies ($f_1$ and $f_2$) and higher harmonics. Furthermore, the mixing frequency technique can differentiate the magnetization of super paramagnetic particles from magnetization of sample holder and matrix. Also, detection coil 130 has high sensitivity in the high frequency region.

Figure 5:
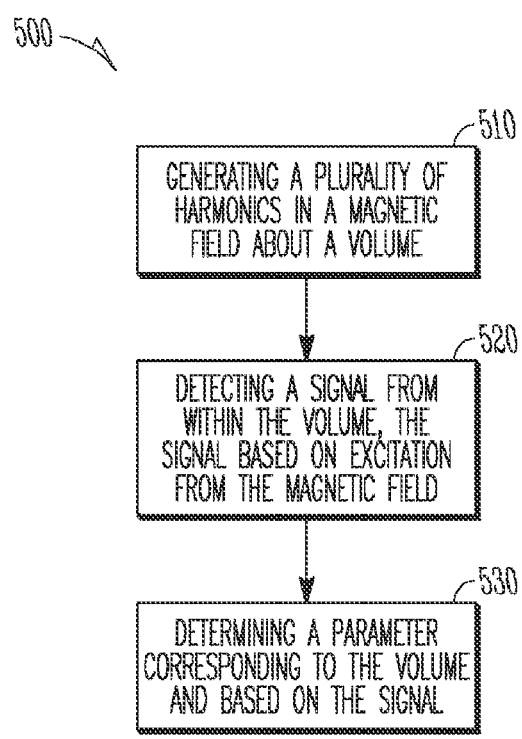
FIG. 5 illustrates a flowchart of a method, according to one example.

As shown in FIG. 5, method 500 can be implemented by an example of the present subject matter. At 510, method 500 includes generating a plurality of harmonics in a magnetic field about a volume. This can include generating a first frequency at a first amplitude and a second frequency at a second amplitude. In another example, this can include generating a swept frequency in the volume. The volume is located interiorly relative to the windings on the device. The harmonics are selected to reduce 1/f noise and measurement noise. In addition, the frequency is selected in view of the sensitivity of detector coil 130. At 520, method 500 includes detecting a signal from within the volume, the signal based on excitation from the magnetic field. In one example, this entails implementing signal processing to discern a parameter. At 530, method 500 includes determining a parameter corresponding to the volume and based on the signal. In one example, this includes determining a resistance measurement for the sensor. In other examples, this entails processing an output signal from the sensor.

Alternative configurations are also contemplated. For example, generating the plurality of harmonics can include delivering excitation at a first frequency and a second frequency, the first frequency different than the second frequency. The first frequency can differ from the second frequency in terms of phase, frequency, amplitude, and time. In one example, generating the plurality of harmonics includes delivering low frequency energy at an amplitude that differs from high frequency energy. Generating the plurality of harmonics can also include delivering low frequency sinusoidal excitation configured to saturate a magnetic nanoparticle in the volume.

A specimen under test can be delivered to the volume using a fluidic channel. A fluidic channel can include a duct, a trench, a tube or other such fluid delivery structure. The magnetic nanoparticle can be bonded or affixed to a target molecule in a manner known as labeling. As such, the labeled molecule can be identified based on the MNP tag affixed thereto. Processing of the signal can include solving equations. For example, in a system of two variables, two equations can be analyzed to derive values for each variable. In addition, processing can include analysis of a delay in phase as between the magnetic field and a detected signal. In one example, processing provides a quantitative assessment of magnetic relaxation. The relaxation time (or frequency) can be evaluated to identify a specimen. In one example, a least squared method is employed to discern meaningful results.

Figure 13:
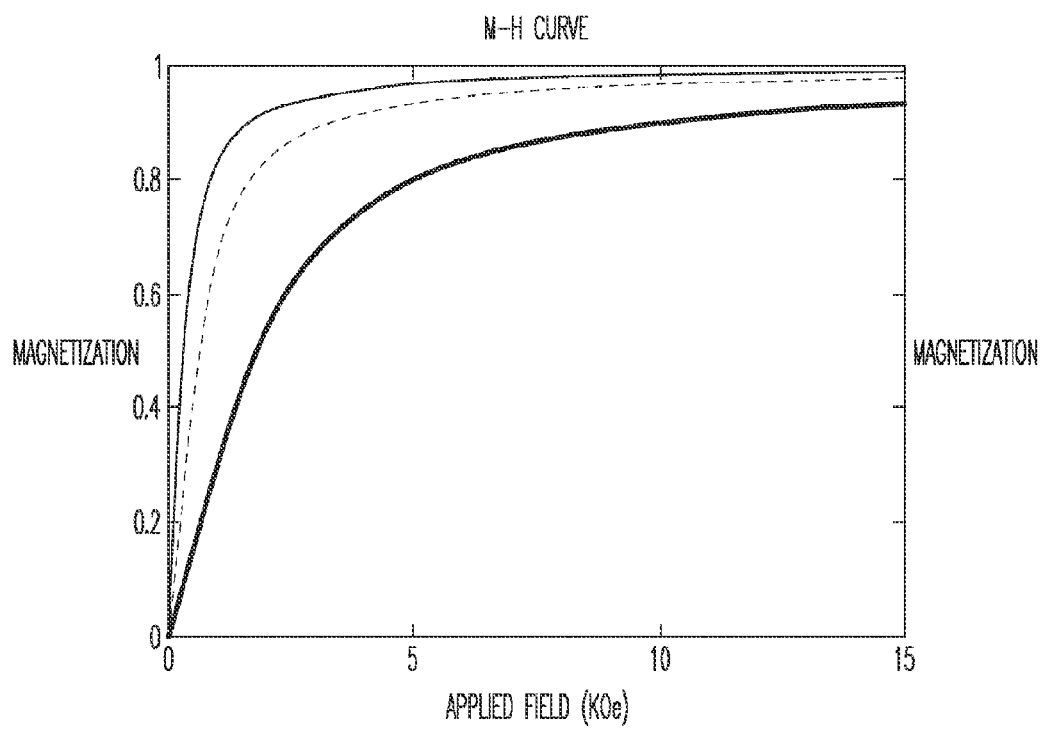
FIG. 13 illustrates M-H curves for three magnetic nanoparticles, according to one example.

In one example, MNPs having different Langevin M-H curves are selected for binding and analysis of a target substance. The different M-H curves (an example of which is shown in FIG. 13) allows particle coloration to discern composition in the sample well.

Real-Time Measurement of Brownian Relaxation of Magnetic Nanoparticles by a Mixing-Frequency Method A detection scheme for real-time Brownian relaxation of magnetic nanoparticles (MNPs) is demonstrated by a mixing-frequency method in this paper. MNPs are driven into the saturation region by a low frequency sinusoidal magnetic field. A high frequency sinusoidal magnetic field is then applied to generate mixing-frequency signals that are highly specific to the magnetization of MNPs. These highly sensitive mixing-frequency signals from MNPs are picked up by a pair of balanced built-in detection coils. The phase delays of the mixing-frequency signals behind the applied field are derived, and are experimentally verified. Commercial iron oxide MNPs with the core diameter of 35 nm are used for the measurement of Brownian relaxation. The results are fitted well with Debye model. Then a real-time measurement of the binding process between protein G and its antibody is demonstrated using MNPs as labels. This study provides a volume-based magnetic sensing scheme for the detection of binding kinetics and interaction affinities between biomolecules in real time.

It will be noted that MNP distribution will vary with exposure concentration Magnetic nanoparticle (MNP) detection for biological and medicinal applications has been achieved by a variety of sensing schemes. The search-coil based sensing technology can be used for point-of-care devices and systems.

Among the attributes are relatively high sensitivity at room temperature, dynamic volume detection (nonsurface binding), intrinsic superiority to measure ac magnetic field, functionality as an antenna for wireless information transmission, and application driven properties such as low cost, portability, and easy of use.

In traditional ac magnetic susceptibility measurement such as Physical Property Measurement System, DynoMag Susceptometer, and Slit Toroid Device, a pair of balanced coils picks up the magnetization of the sample under an ac magnetic field and a lock-in amplifier or impedance analyzer is used to detect the complex ac susceptibility. However, these methods suffer from high background fluctuation due to the thermal and mechanical instability of the coils, as well as the magnetic moment contribution from sample matrix (e.g., water) or container (e.g., plastic tube). Given the small amount of MNPs sample in the paramagnetic or diamagnetic environment, the background is a significant portion of the overall signal. In contrast, a mixing-frequency method can be used to detect the nonlinear magnetization of MNPs per testing sample by measuring the amplitude of the mixing frequency signals and thereby avoid the high noise at the fundamental frequencies. A magnetic field with low frequency (e.g., f2=10 Hz) and large amplitude drives the MNPs into their nonlinear saturation region periodically. Another magnetic field with higher frequency (e.g., f1=20 kHz), and with a relatively small amplitude due to the inductance of excitation coil, is used to transfer the nonlinearity into the mixing frequency signals, such as f1+2f2, (20.02 kHz). In this higher frequency region, the detection coil has higher output voltage amplitude, and the measurement system has lower 1/f noise, thus the mixing-frequency method can greatly improve the signal-to-noise ratio.

A search coil based susceptometer can be used to measure the real-time Brownian relaxation of MNPs by the mixing-frequency method. Traditionally, the changes in Brownian relaxation before and after the binding events were experimentally shown by searching the peak of imaginary susceptibility in the entire frequency domain. This method faces a challenge for a realtime measurement.

Phase delay of the mixing-frequency signal can be measured along the frequency of one of applied sweeping ac fields. The phase delay can be related to the relaxation time of MNPs, which enables monitoring the Brownian relaxation process of MNPs in real time. Superparamagnetic nanoparticles with small sizes can be used for biological applications to avoid the aggregation as well as any negative influence without external field. Its magnetization curve can be expressed as follows:

$$M = M_s * \mathcal{L}\left(\frac{m_0 \mu_0 H}{k_B T}\right)$$

where $M_s$ is the saturation magnetization, $m_0$ is the magnetic moment of a single particle, $\mu_0$ is the permeability of vacuum, H is the applied field, $k_B$ is the Boltzmann constant, T is the absolute temperature, and L is the Langevin function.

$$\mathcal{L}(x) = \coth(x) - \frac{1}{x}. \quad (2)$$

Two sinusoidal magnetic fields are applied simultaneously as follows: one with low amplitude $A_1$, high frequency $f_1$, written as $A_1 \cos(2\pi f_1 t)$; the other with high amplitude $A_2$, low frequency $f_2$, written as $A_2 \cos(2\pi f_2 t + \theta_2)$. The sum of these two fields (H) is transferred to magnetization (M) by Langevin function. Taylor Expansion near zero magnetization shows that, besides the linear response, the major mixing components are as the following:

$$[A_1\cos(2\pi f_1 t) + A_2\cos(2\pi f_2 t)]^3 = \ldots + \frac{3}{4}A_1 A_2^2 \cos[2\pi(f_1 \pm 2f_2)t] + \ldots$$

There are two relaxation mechanisms for MNPs. The physical rotation of particle in the viscous medium is called Brownian relaxation, and magnetic dipole flipping inside a stationary particle is called Néel relaxation. Brownian relaxation depends on an effective hydrodynamic volume. Néel relaxation depends on magnetic volume. The total relaxation process is a parallel model of these two relaxation schemes, but Brownian relaxation dominates when MNP's diameter is large, e.g., iron oxide MNP's diameter is larger than 20 nm:

$$\tau_{total} = \tau_B = \frac{3\eta V_B}{k_B T},$$

where η is the viscosity of the carrier or matrix fluid and $V_H$ is the effective hydrodynamic volume of MNP.

When the frequency of ac applied field is low, the particles' magnetization can follow the excitation field tightly, and the susceptibility χ is a real number. As the excitation frequency increases, the particles' magnetization cannot follow the excitation field, and the relaxation processes introduce a phase in the complex ac susceptibility. The relationship between relaxation time τ and phase φ of ac susceptibility can be calculated using Debye model.

$$\chi(\omega) = \frac{\chi_0}{1 + j\omega\tau} = \frac{\chi_0}{1 + (\omega\tau)^2} e^{-j\tan^{-1}(j\omega\tau)} = |\chi|e^{j\varphi}.$$

Where $\chi_0$ is the static susceptibility and ω is the angular frequency. Assuming the particles' magnetization has a phase delay $\phi_1$ to the high frequency field and a phase delay $\phi_2$ to the low frequency field, the mixing-frequency component of magnetization becomes as follows:

$$[A_1\cos(2\pi f_1 t - \varphi_1) + A_2\cos(2\pi f_2 t - \varphi_2)]^3 =$$
$$\ldots + \frac{1}{2}A_1 A_2^2 \cos[2\pi(f_1 + 2f_2)t - \varphi_1 - 2\varphi_2] + \ldots$$

The total relaxation phase $\phi_1 + 2\phi_2$ can therefore be determined by measuring the phase of the mixing frequency at $f_1 + 2f_2$. If one frequency (e.g. $f_2$) is fixed, and the other frequency (e.g. $f_1$) is swept, the relaxation phase $\phi_1 + 2\phi_2$ along $f_1$ will show the relationship between $\phi_1$ and $f_1$. Either one of $f_1$ and $f_2$ can be swept depending on whether high frequency region or low frequency region is of interest.

An example of the present subject matter includes two excitation coils that generate 10 Hz ac field with 100 Oe amplitude and 20 kHz ac field with 10 Oe amplitude, respectively. One pair of pick up coils with differentially wounded 500 rounds is installed. An instrumentation amplifier connected to a digital acquisition card (DAQ) can be used for the signal amplification.

A program for the instrument control and a program for signal processing are installed in the computer for controlling the whole setup. Commercially available iron oxide MNPs samples can be used for Brownian relaxation study: MNPs with 35 nm core size, 4 nm oleic acid, and amphiphilic polymer coating, 0.1 ml, 5 mg/ml in H2O-carboxylic acid solution, IPG35 SHP35 conjugated with around 10 nm protein G layer, 0.1 ml, 1 mg/ml, and IPG35-Ab IPG35 conjugated with around 10 nm Goat anti-Human IgG an antibody isotype of mammals HRP with ratio 1:100, 0.1 ml, 1 mg/ml.

Particle Size Distributions are Measured by a Dynamic Light Scattering (DLS) Instrument All the three samples are from the same batch of 35 nm iron oxide MNP core, so the wide hydrodynamic size distribution of IPG35-Ab shows that IPG35 binds with antibodies in a range of binding affinity. This can also be confirmed by an independent gel electropherosis measurement.

The MNPs' phase delay can be measured for these three samples under ac fields. Phase delay of the mixing-frequency signal is measured by scanning the frequency of $f_1$ up to 10 kHz. To prevent any temperature drift due to joule heating of the coil, tone bursts are applied rather than continuous ac field.

The experimental results are fitted by the Debye model presented earlier. Since the particles are not monodispersed, the total susceptibility comes from the contributions of all MNPs with various sizes. A Debye model with the superposition of MNPs' hydrodynamic size distribution is a good fit, although it is argued that Debye model is only valid for small-amplitude low-frequency applied ac field and a high frequency susceptibility $\chi$ is needed for the Debye fitting.

The binding process of the antibody to protein coated MNPs solution is detected by monitoring real time relaxation. Instead of the time-consuming whole frequency scan, the frequency $f_1$ is fixed at a 4 kHz due to the high signal-to-noise ratio around this frequency region (detection coil is not sensitive in lower frequency region while MNP has low ac susceptibility in higher frequency region). 0.05 ml antibody (goat antihuman IgG HRP conjugated, 5 mg/ml) is dropped onto 0.1 ml IPG35 sample. The antibody sample will then diffuse slowly into IPG35 solution, and gradually bind to protein G on the surface of MNPs, until protein G binding sites on MNPs are saturated with antibody and has the same hydrodynamic size distribution as the standard IPG35-Ab sample prepared. On the surface of IPG35 MNPs where protein G is not attached, hydrophilic polyethyleneglycol (PEG) is coated to block nonspecific binding. Both the phase transition and amplitude transition during protein G-antibody binding process are recorded. After the antibody is added to the sample at the 50th second, the detected amplitude of the mixing frequency is dropping sharply because the sample gets diluted away from the center of the detection coil, and also binding events will decrease the MNPs' susceptibility as shown earlier.

The amplitude of susceptibility has been used to determine particle clustering and binding but it is heavily affected by the spatial distribution and concentration of the MNPs. In contrast, the phase information records the binding process reliably. As shown, the antibody solution is added into IPG35 solution at 50th second. As antibodies diffuse into IPG35 solution and bind with MNPs, the phase delay of magnetization then begins to increase, and gradually reaches a plateau which is very close to that of the standard IPG35-Ab.

There are two sources for the relatively large noise for the real time phase delay measurement. Since the MNPs concentration decreases due to dilution, the output signal amplitude decreases and the phase delay measurement suffers from smaller signal-to-noise ratio. Another noise source is from the digitization device when measuring the small mixing frequency signals buried in the large carrier frequency signals. Dynamic carrier tone cancellation scheme can be implemented to reduce the noise and this is in progress. Another method to determine the binding process is to use the ratio of higher harmonics from the nonlinear magnetization.

When hydrodynamic size increases, the MNPs relax slower and are less likely to reach saturation region, thus the nonlinearity of magnetization changes. The ratio between amplitude at $f_1+2f_2$ and at $f_1+4f_2$ is tracked along with phase measurement during the binding process. The results of amplitude ratio are much less sensitive than the phase measurement, and the results are much harder to be interpreted into binding properties. However, the amplitude ratio of higher harmonics contains rich information of nonlinear magnetization and may complement phase measurement to study the MNPs.

In summary, the present subject matter includes a technique to detect the real-time relaxation of MNPs by using the mixing-frequency method.

In one experiment, three MNPs were colorized in a simulation and two MNPs were colorized. Data shows that colorization can be using different static magnetic static fields, using a different frequency, and using phase information.

Figure 6A:
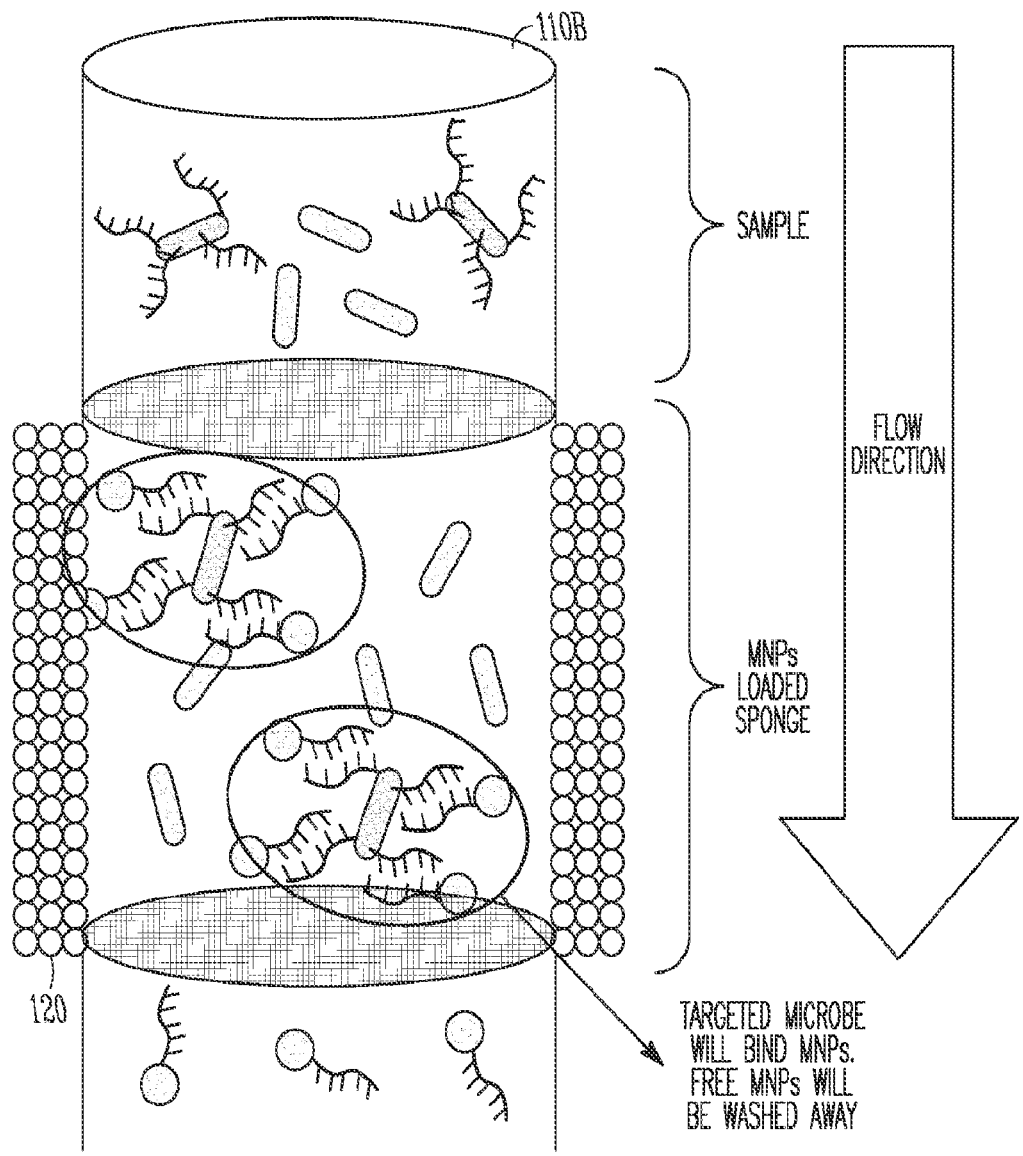
FIG. 6 illustrates a device, according to one example.
Figure 6B:
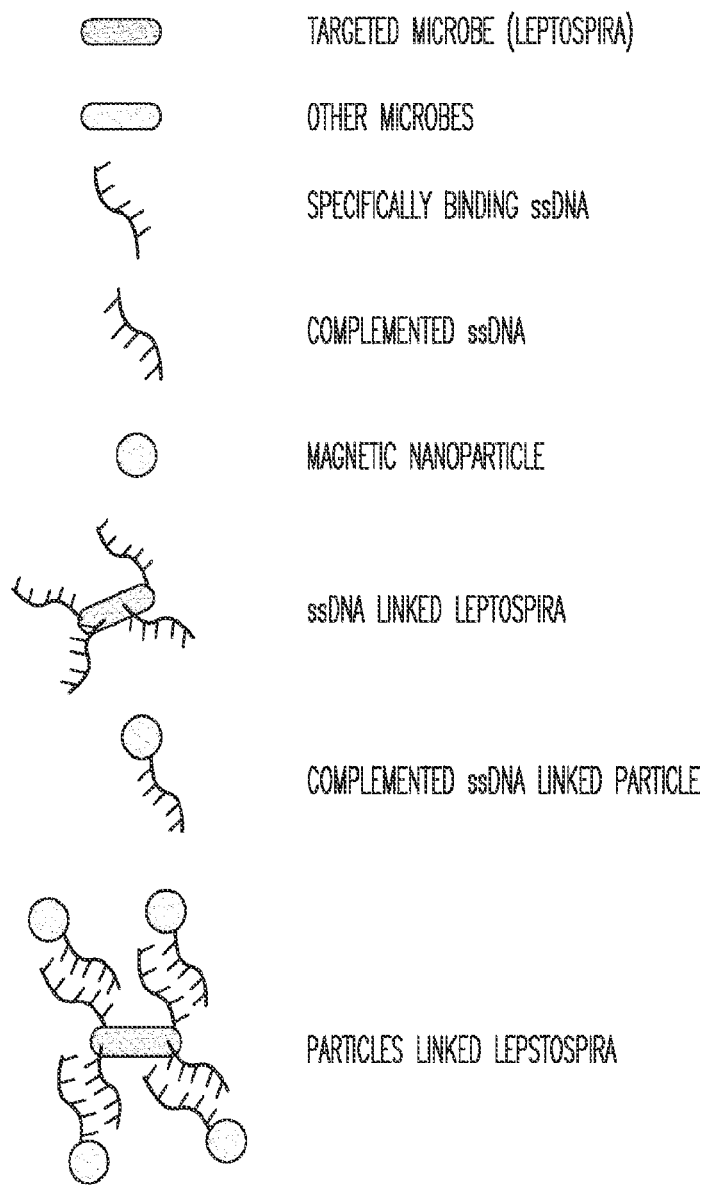

FIG. 6A illustrates a sponge diagnostic schematic. In the figure, the sample container is depicted as a cylindrical member having a plurality of windings 120 around a circumference. The windings are directed to exciting a specimen in the volume of the cylinder. In the figure, the sample is located in portion 110B located above the height of the excitation coils. A portion aligned with the excitation coil is filled with a loaded sponge and includes MNPs. As shown in the figure, the sample container includes a sponge. The sponge is selected to facilitate binding of the targeted microbe and MNPs. FIG. 6B includes a legend indicating that targeted microbes and other elements are selected and identified using MNP-loaded sponge. Fluid flow direction is indicated in a downward direction as shown by an arrow in FIG. 6A.

Figure 7:
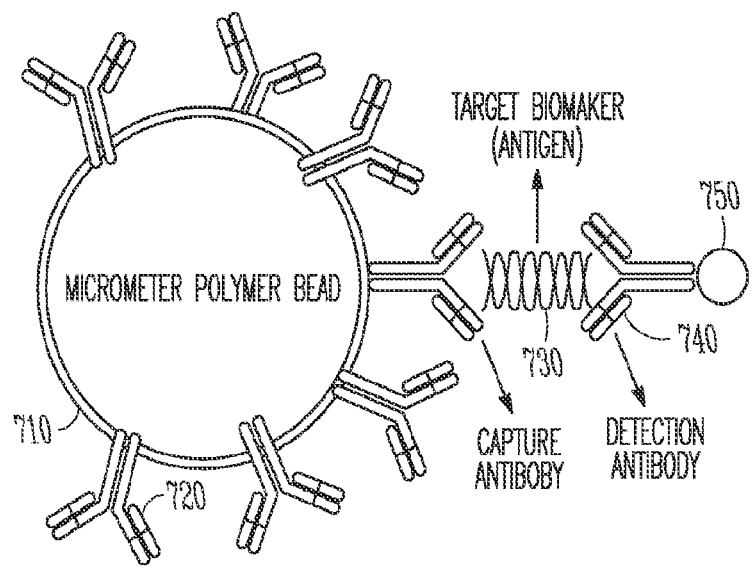
FIG. 7 illustrates a polymer bead, according to one example.

FIG. 7 illustrates a polymer bead configured for detection and identification according to one example of the present subject matter. As shown, polymer bead 710 is bound to a plurality of capture antibodies 720. The capture antibodies have structures that are configured to receive a target molecule. In the figure, a capture antibody 720 is shown coupled to a target biomarker (antigen) 730. At one end, target biomarker 730 is selectively coupled to the capture antibody. At an opposing end of target biomarker 730, a detection antibody 740 is bound to the target biomarker (antigen). In addition, a leg of the detection antibody is coupled to a magnetic nanoparticle. The presence of the antigen will link an MNP to the polymer bead, thus suppressing Brownian rotation. Polymer bead 710 is but one example, and depending on the task requirements, a search coil as described herein can include any number of different polymer beads, with different beads having an affinity for different molecules.

Figure 8:
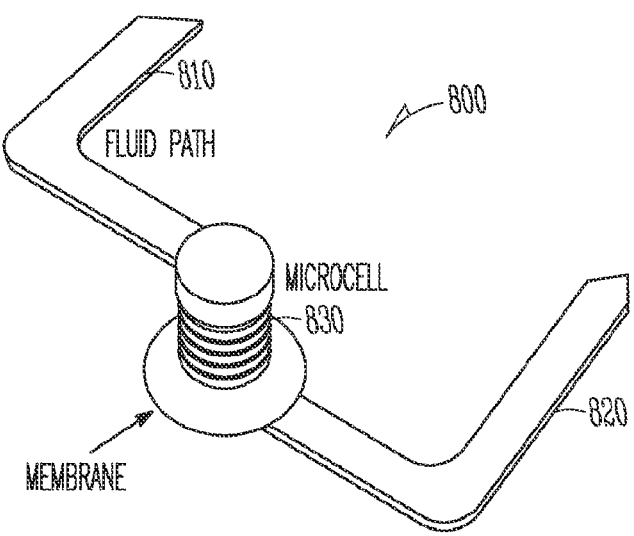
FIGS. 8 and 9 illustrate devices according to various examples.
Figure 9:
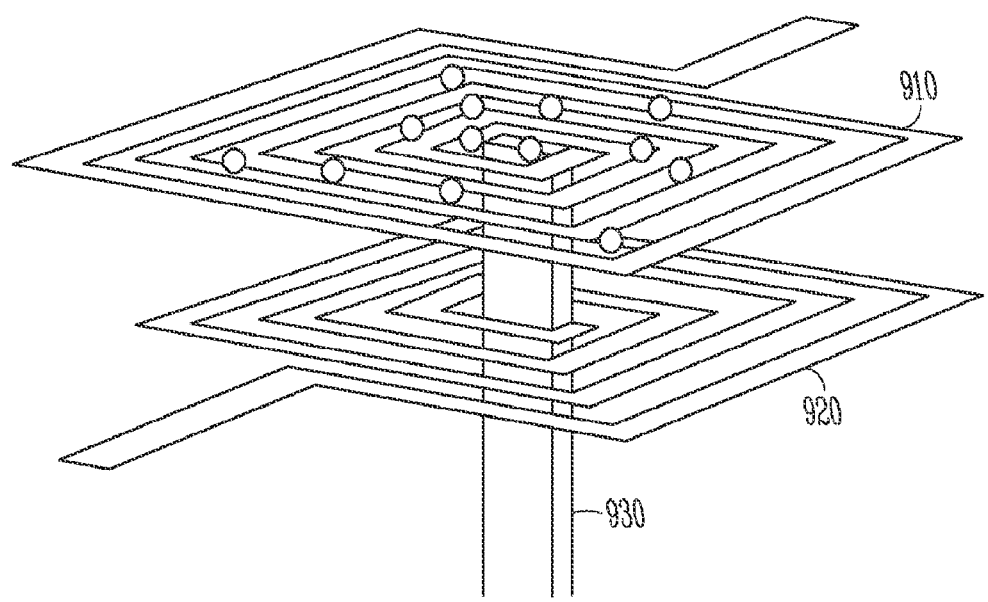

FIGS. 8 and 9 illustrate other device configurations. In FIG. 8, the device is shown to include what looks like a small number of windings on a small spindle. Fluid path 810 and fluid path 820 (intake and output, for example) are provided to carry fluid through the volume of the device. Coils 830 on the body of device 800 can be used to deliver one or more excitation signals. FIG. 9 illustrates an example fabricated using a multilayer printed circuit board and is configured for presentment on television. The relatively planar windings shown in FIG. 9 can provide static excitement to a specimen in the sample container well. Windings 910 and windings 920 may be wound in a balanced manner. Fluidic channel 930 can be configured to carry a specimen to the test site.

Figure 10:
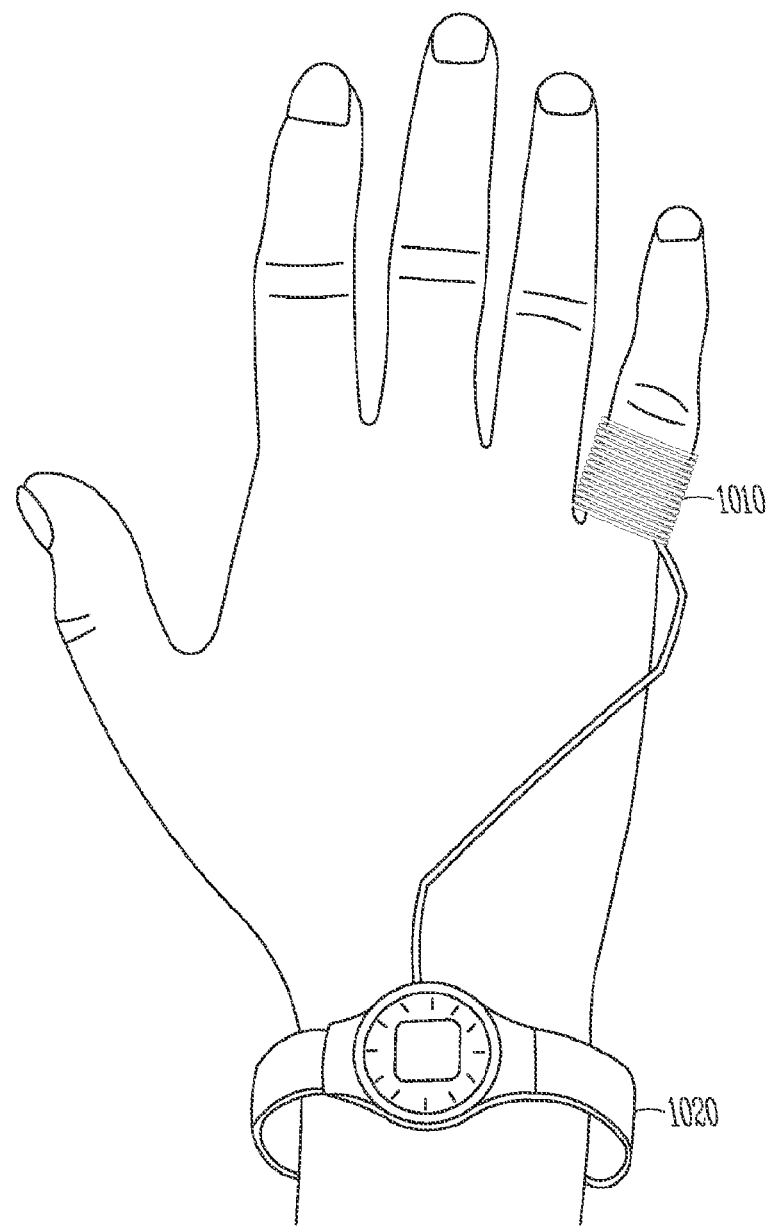
FIG. 10 illustrates a body-worn external device, according to one example.

FIG. 10 includes a personal test or diagnostic device. In the figure, coil 1010 includes a plurality of windings. The windings of coil 1010 can provide excitation to a finger of a wearer. As such, coil 1010 can provide data as to biological elements associated with or travelling within the tissue of a wearer. In addition, coil 1010 can be configured to provide an audio output message. Wrist-worn device 1020 is coupled to coil 1010 by a wired coupling. The wired coupling enables coil 1010 to have access to a larger database with more resources. The line between coil 1010 and device 1020 can be configured to deliver an excitation signal or configured to convey a detected signal based on presence or absence of a MNP. Device 1020, in one example, includes telemetry circuitry to enable wide area access and delivery of the system.

Figure 11:
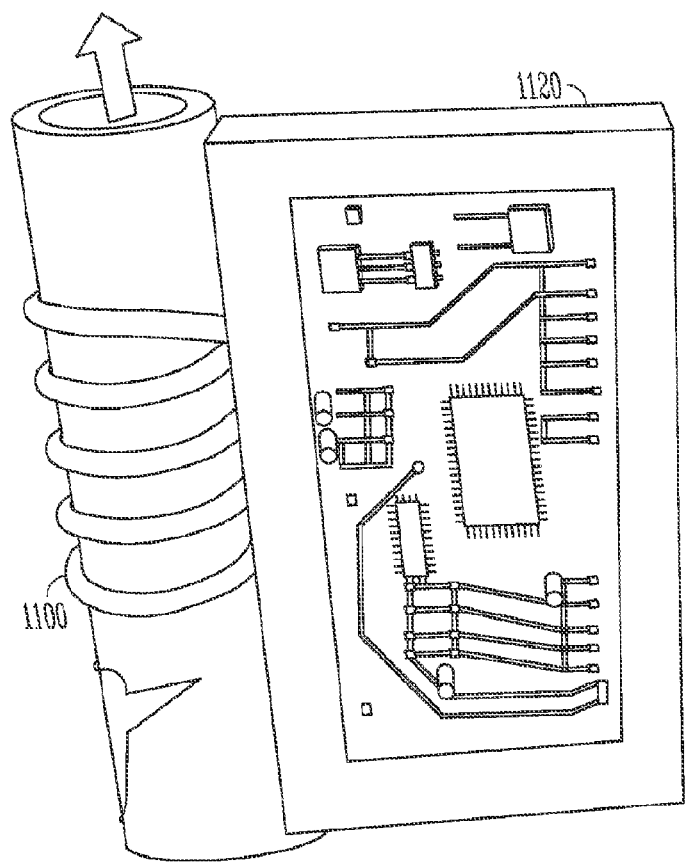
FIG. 11 illustrates an implantable device, according to one example.

FIG. 11 illustrates an implantable device. In the figure, coils 1100 encircle a blood vessel or other body fluid duct. Fluid flow is shown by the small arrow in the figure. In addition, module 1120 is coupled to coils 1100. Module 1120 can include data storage, instruction storage, an amplifier, a data converter, a transceiver, a processor or other elements configured to provide sensing and coloring functions as described herein.

Figure 12:
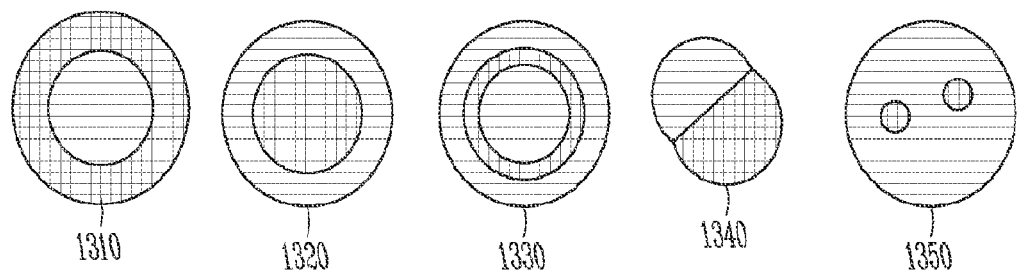
FIG. 12 illustrates examples of magnetic nanoparticles.

Examples of assorted magnetic nanoparticles are shown in FIG. 12. Magnetic nanoparticle 1310 includes a first arrangement of core and shell elements and MNP 1320 includes a second arrangement. Magnetic nanoparticle 1330 includes a multi-shell example. Magnetic nanoparticle 1340 includes a pair of semispherical elements and MNP 1350 includes a pair of nodes embedded in a different element.

FIG. 13 illustrates M-H curves for three magnetic nanoparticles, according to one example. For three kinds of superparamagnetic nanoparticles with different Langevin M-H curves, application of three AC fields can be used to differentiate the nanoparticles based on their magnetic response. Langevin M-H curves for three different nanoparticles are shown in FIG. 13.

Figure 14:
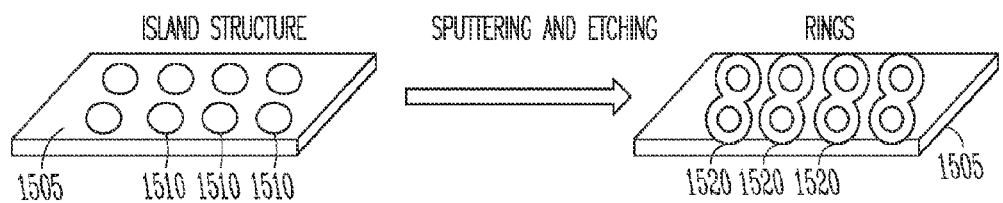
FIG. 14 illustrates examples of magnetic nanoparticles formed as rings.

FIG. 14 illustrates examples of magnetic nanoparticles formed as rings.

Nanometer scale magnetic rings may provide a tunable magnetic behavior. Ring diameter, ring aspect ratio and consisting materials are factors that can be changed to pursue a desired magnetic property.

Nanorings, such as those shown in FIG. 14, can be fabricated by various methods. In one example, material is deposited onto substrates to form islands by selecting surface energy of the two. In another example, sputtering ring material is used to form a thin layer and etch. Around the island where nucleation first occurs will have the thickest material and remains in a ring geometry after etching. Incomplete nanorings are shown at 1510 on substrate 1505 and, on substrate 1505 on the right side, completed nanorings 1520 are shown.

In another method, nanorings are fabricated by depositing ring material onto a substrate to form a thin film. In addition, place block copolymer rings onto the metal film and use ion etching to remove extra film material.

Figure 15:
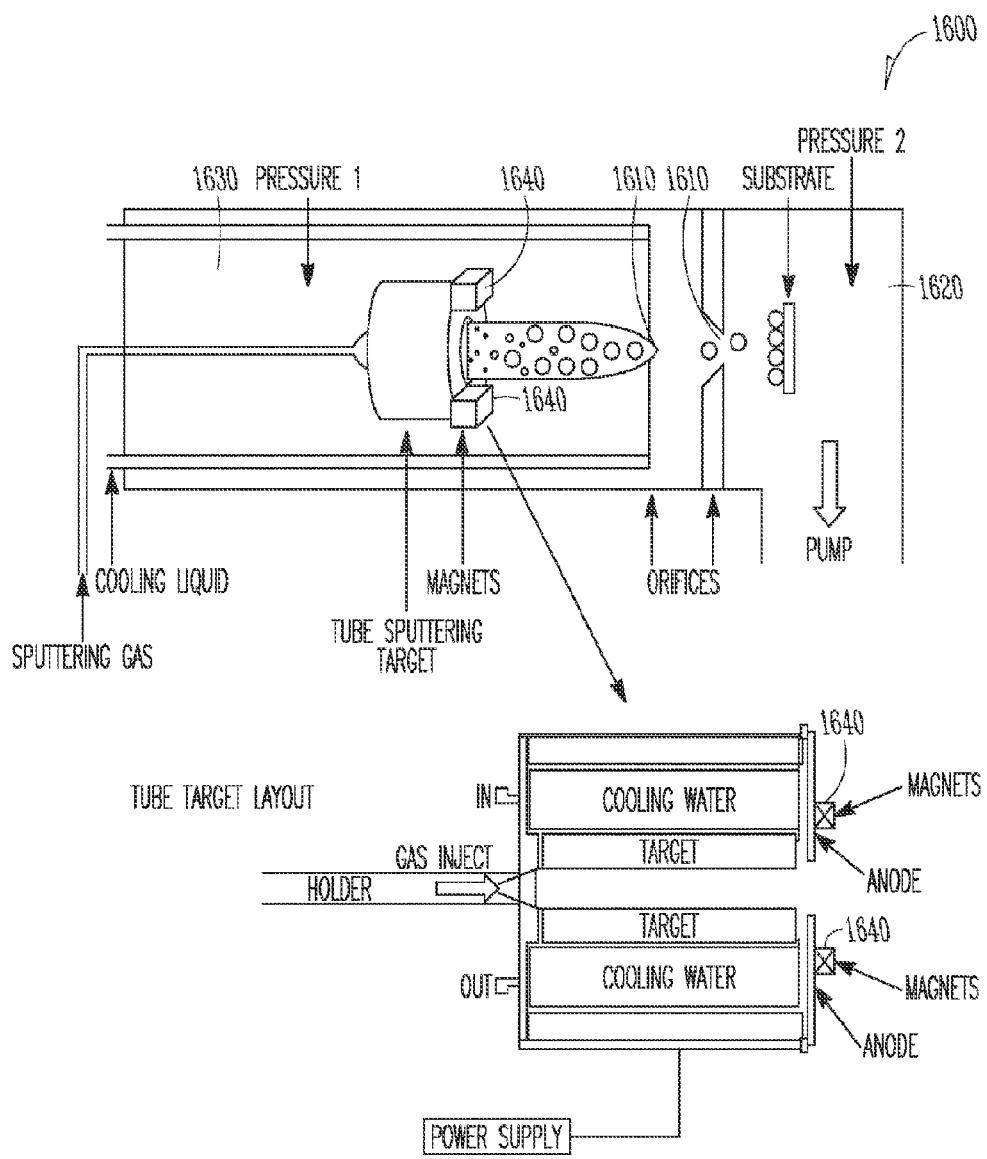
FIG. 15 illustrates an example of a system for fabricating magnetic nanoparticles.

FIG. 15 illustrates nanofabrication system 1600, according to one example. As noted, pressure in region 1630 can be modulated to produce desired effects. In one example, the pressure is between 200 and 900 mTorr. Pressure in region 1620 is typically under 1 mTorr. Dimensions and profile of orifice 1610 can also be controlled to produce a desired effect. Furthermore, the field strength of magnets 1640 can be tailored for a particular purpose.

MNP Colorization

Various magnetic nanoparticles having different magnetic behavior can be fabricated. The different behaviors are associated with magnetic coloring.

Magnetic nanoparticles with different magnetization behavior can be used as an identification signal.

A variety of magnetic nanoparticles having a selectable size, composition control, heterostructure, different morphology, etc., can be fabricated. These nanoparticles possess different magnetic properties and are able to be differentiated through their AC response.

Among other things, colorization of nanoparticles enables:

a) magnetic nanoparticles with magnetic coloring effect that can be applied in related biomedical applications, e.g. low cost and small-size or handheld magnetic cytometry (to sort, identify, and quantify the cells, proteins, or other molecules);

b) more than ten colors c) identify multiple food contaminations, environment damage.

Magnetic nanoparticles can be non-toxic and exhibit high-magnetic-moment, and are tunable for selected magnetic behavior which can provide a differentiated AC response;

Superparamagnetic nanoparticles follow Langevin law.

The ability to access magnetic nanoparticles with different M-H loops or Néel relaxation times enables "magnetic colors" to allow bio-labels for disease detection. Among other things, a magnetic signal is unaffected by the background from biological matters. In addition, a magnetic signal can penetrate tissue with negligible side-effects and Fe-based magnetic nanoparticles have improved biocompatibility compared to some quantum dots.

Others have attempted to fabricate magnetic particles. A top-down fabrication technique (based on lithography) has obstacles in scaling down the feature size with reasonable cost. In addition, the particle size is over 100 nm or larger. This dimension scale is not suitable for binding with molecules to be detected. Furthermore, the nanostructures may contain toxic materials unsuitable for biological use in order to achieve particular structure controlled magnetic property. In addition, chemical synthesis methods are able to provide very small magnetic nanoparticles, however, the process introduces other chemical residuals on the surface of the nanoparticles, which are difficult to remove.

An example of the present subject matter entails fabricating high-magnetic moment nanoparticles having a magnetic coloring effect. Size, composition, heterostructure and morphology of nanoparticles are designed and controlled to give different magnetic behavior. In one example, the materials have high saturation magnetization. A synthesis method can be implemented using physical gas condensation or other fabrication technique.

The magnetic moment of a nanoparticle will change with a change in size. The magnetic behavior will differ among each size category according to the Langevin theory. In one example, a high saturation magnetization material, such as FeCo, is selected. FeCo nanoparticles of differing size can be synthesized by physical gas condensation. Different sizes can be achieved by selection and control of the gas flow, sputtering current, and magnetic field strength.

The specific magnetization change verses applied field for FeCo nanoparticles of different size shows observable differences. In addition, the composition of the nanoparticles can be changed. $Fe_xCo_{1-x}$ nanoparticles with different Fe:Co composition ratio can be fabricated by physical gas condensation method. Furthermore, magnetization and magnetic anisotropy differences caused by alloy composition change can play a role in the consequent loop difference. Examples of fabrication conditions are as follows:

|  | $Fe_{10}Co_{90}$ | $Fe_{40}Co_{60}$ | $Fe_{70}Co_{30}$ |
|---|---|---|---|
| Sputtering pressure (mTorr) | 600 | 450 | 300 |
| Sputtering current (A) | 0.5 | 0.5 | 0.5 |
| Surface magnetic field strength (Oe) | 750 | 650 | 630 |
| Crystal structure | fcc | bcc | Bcc |
| Anisotropy constant (ergs/cm$^3$) | $5 \times 10^6$ | $3 \times 10^6$ | $1 \times 10^6$ |

Magnetic nanoparticles having heterostructure can lead to a special spin configuration confined in the nano-dimension. This can lead to a more tunable M-H behavior. This can be fabricated by the gas phase synthesis method. Material choice and control of diffusion on the atomic scale can produce results.

The core-shell structure can be demonstrated by an EDX line scan across a single Co—Au nanoparticle synthesized by physical gas condensation method. In one example, the core is rich in Co and the shell is rich in Au. At room temperature, the nanoparticles show superparamagnetic behavior, which is consistent with Au covered Co.

Other types of heterostructure are also achievable through gas phase synthesis. These heterostructures can enrich the archive of magnetic colors. In one example, fabrication conditions include sputtering gas flow at 9.4 sccm and sputtering pressure at 200 mTorr. In another example, the fabrication conditions include sputtering gas flow at 16.7 sccm and sputtering pressure at 363 mTorr.

In one example, specific control of interparticle dipolar interaction through cluster ensemble type of heterostructure can provide a novel way to generate multiple magnetic colors. For example, the magnetization process of one small cluster is subject to influence from clusters in near proximity. It may be found that cluster ensemble types of particles are able to give differentiated magnetic behavior.

In one example, a tube target is provided in the gas phase deposition system. In one example, a tube target is used with a $Fe_{70}Co_{30}$ nanoparticles fabricated under conditions including: sputtering $Ar_2$ gas flow 21 sccm; sputtering gas pressure 400 mTorr, and sputtering current 0.6 A.

Morphology control of nanoparticles can modify the magnetic property in terms of the shape anisotropy, which is affected by the aspect ratio. In one example, magnetic energy barrier can be tuned to give different Néel relaxation time. Relaxation time difference is reflected by the phase of magnetization subject to AC field.

In sum, magnetic nanoparticle colors can be achieved by tuning magnetic behavior of nanoparticles. The colors are candidate labels or markers for detection, for example, multiple biological diseases diagnosis.

In one example, a magnetic flow cytometry system can be prepared. The system can include different size cells and each bonded to different nanoparticles. By using various combinations of nanoparticles, many different colors are available.

Various Notes & Examples

Example 1 includes a device having an excitation coil, a detector coil, and a processor. The excitation coil is aligned about a volume. The excitation coil is configured to carry a first and second biasing current and generate a magnetic field in the volume. The detector coil is configured to generate an electrical signal based on a detected field within the volume. The detected field is based on the magnetic field. The processor is configured to generate data based on the electrical signal.

In Example 2, the subject matter of Example 1 can optionally include wherein the first biasing current is configured to generate a low frequency modulation of the magnetic field.

In Example 3, the subject matter of one or any combination of Examples 1 and 2 can optionally include wherein the first biasing current is configured to generate a high frequency modulation of the magnetic field.

In Example 4, the subject matter of one or any combination of Examples 1 to 3 can optionally include a fluid channel in fluid communication with the volume.

In Example 5, the subject matter of one or any combination of Examples 1 to 4 can optionally include wherein the fluid channel includes a biological duct.

In Example 6, the subject matter of one or any combination of Examples 1 to 5 can optionally include wherein the processor includes a wireless transceiver.

In Example 7, the subject matter of one or any combination of Examples 1 to 6 can optionally include wherein the detector coil includes a pair of complementary windings.

Example 8 includes subject matter comprising a method including generating a plurality of harmonics in a magnetic field about a volume, detecting a signal from within the volume, and determining a parameter. The signal is based on excitation from the magnetic field. The method includes determining a parameter corresponding to the volume and based on the signal.

In Example 9, the subject matter of Example 8 can optionally include wherein generating the plurality of harmonics includes delivering excitation at a first frequency and a second frequency, the first frequency different than the second frequency.

In Example 10, the subject matter of one or any combination of Examples 8 and 9 and optionally wherein generating the plurality of harmonics includes delivering low frequency sinusoidal excitation configured to saturate a magnetic nanoparticle in the volume.

In Example 11, the subject matter of one or any combination of Examples 8 to 10 and optionally including delivering a specimen to the volume using a fluidic channel.

In Example 12, the subject matter of one or any combination of Examples 8 to 11 and optionally including labeling using a magnetic nanoparticle before delivering.

In Example 13, the subject matter of one or any combination of Examples 8 to 12 and optionally wherein determining the parameter includes processing to evaluate a plurality of equations.

In Example 14, the subject matter of one or any combination of Examples 8 to 13 and optionally wherein determining the parameter includes processing to evaluate a delay in phase as to the magnetic field and the detected signal.

In Example 15, the subject matter of one or any combination of Examples 8 to 14 and optionally wherein determining the parameter includes processing to evaluate magnetic relaxation.

In Example 16, the subject matter of one or any combination of Example 8 to 15 and optionally wherein determining the parameter includes processing to determine an estimate using a least squares method.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A device comprising:
   an excitation coil aligned about a volume, the excitation coil configured to carry a first and second biasing current and generate a magnetic field in the volume;
   a detector coil configured to generate an electrical signal based on a detected field within the volume, the detected field based on the magnetic field; and
   a processor configured to generate data based on the electrical signal, wherein the data is determined by a phase delay between the detected field and the magnetic field of the excitation coil.

2. The device of claim 1 wherein the first biasing current is configured to generate a low frequency modulation of the magnetic field.

3. The device of claim 1 wherein the second biasing current is configured to generate a high frequency modulation of the magnetic field.

4. The device of claim 1 further including a fluid channel in fluid communication with the volume.

5. The device of claim 4 wherein the fluid channel includes a biological duct.

6. The device of claim 1 wherein the processor includes a wireless transceiver.

7. The device of claim 1 wherein the detector coil includes a pair of complementary windings.

8. The device of claim 1 wherein the phase delay correlates to a relaxation time of a specimen in the volume.

9. A method comprising:
   generating a plurality of harmonics in a magnetic field about a volume, wherein generating includes delivering excitation to an electrical winding of a coil;
   detecting a signal from within the volume, the signal based on excitation from the magnetic field; and
   determining a parameter corresponding to the volume and based on the signal, and wherein determining the parameter includes processing to evaluate a delay in phase as to the magnetic field provided by the coil and the magnetic field as to the detected signal.

10. The method of claim 9 wherein generating the plurality of harmonics includes delivering excitation at a first frequency and a second frequency, the first frequency different than the second frequency.

11. The method of claim 9 wherein generating the plurality of harmonics includes delivering low frequency sinusoidal excitation configured to saturate a magnetic nanoparticle in the volume.

12. The method of claim 9 further including delivering a specimen to the volume using a fluidic channel.

13. The method of claim 12 further including labeling a target molecule of the specimen using a magnetic nanoparticle before delivering.

14. The method of claim 9 wherein determining the parameter includes processing to evaluate a plurality of equations.

15. The method of claim 9 wherein determining the parameter includes processing to evaluate magnetic relaxation.

16. The method of claim 9 wherein determining the, parameter includes processing to determine an estimate using a least squares method.

17. The method of claim 9 wherein delivering excitation to the electrical winding includes applying a swept frequency.

* * * * *

UNITED STATES PATENT AND TRADEMARK OFFICE
CERTIFICATE OF CORRECTION

PATENT NO. : 9,778,225 B2
APPLICATION NO. : 13/885384
DATED : October 3, 2017
INVENTOR(S) : Wang et al.

It is certified that error appears in the above-identified patent and that said Letters Patent is hereby corrected as shown below:

In the Specification

In Column 1, Lines 29-31, delete "This invention was made with government support under award number 1717-522-6686 from National Science Foundation. The government has certain rights in this invention." and insert --This invention was made with government support under CBET0730825 awarded by the National Science Foundation. The government has certain rights in the invention.-- therefor Signed and Sealed this
Fourteenth Day of May, 2024

Katherine Kelly Vidal
*Director of the United States Patent and Trademark Office*